United States Patent
Esch et al.

(10) Patent No.: US 6,210,363 B1
(45) Date of Patent: Apr. 3, 2001

(54) METHODS AND DEVICES FOR OCCLUDING A VESSEL AND PERFORMING DIFFERENTIAL PERFUSION

(75) Inventors: Brady Esch, San Jose; Janine Robinson, Half Moon Bay; John Macoviak, La Jolla; Wilfred Samson, Saratoga; Eric Olsen, Los Gatos, all of CA (US)

(73) Assignee: Cardeon Corporation, Cupertino, CA (US)

( * ) Notice: Subject to any disclaimer, the term of this patent is extended or adjusted under 35 U.S.C. 154(b) by 0 days.

(21) Appl. No.: 09/256,263

(22) Filed: Feb. 23, 1999

(51) Int. Cl.⁷ .................................................. A61M 29/00

(52) U.S. Cl. .......................................... 604/96; 604/99.02

(58) Field of Search ................................ 604/96, 500, 4, 604/99.02, 28; 128/634

(56) References Cited

U.S. PATENT DOCUMENTS

| | | | |
|---|---|---|---|
| 3,995,623 | * 12/1976 | Blake et al. | 600/381 |
| 3,996,938 | 12/1976 | Clark, III | 128/348 |
| 4,173,981 | 11/1979 | Mortensen | 128/348 |
| 4,494,531 | 1/1985 | Gianturco | 128/1 R |
| 4,527,549 | 7/1985 | Gabbay | 128/1 |
| 4,650,466 | 3/1987 | Luther | 604/95 |
| 4,661,094 | 4/1987 | Simpson | 604/53 |
| 4,721,115 | * 1/1988 | Owens | 128/713 |
| 4,723,549 | 2/1988 | Wholey et al. | 128/344 |
| 4,741,328 | 5/1988 | Gabbay | 128/1 |
| 4,793,348 | 12/1988 | Palmaz | 128/325 |
| 4,817,600 | 4/1989 | Herms et al. | 128/303 |
| 4,856,529 | * 8/1989 | Segal | 128/661.08 |

(List continued on next page.)

FOREIGN PATENT DOCUMENTS

| | | | |
|---|---|---|---|
| 86201487 | 8/1986 | (EP) | A61M/25/00 |
| WO 97/17100 | 5/1997 | (WO) | A61M/29/00 |
| WO 97/42879 | 11/1997 | (WO) | A61B/17/00 |
| WO 98/02084 | 1/1998 | (WO) . | |
| WO 98/24377 | 6/1998 | (WO) | A61B/17/22 |
| WO 99/04848 | 2/1999 | (WO) | A61M/29/00 |

OTHER PUBLICATIONS

Barbut et al., "Determination or Size of Aortic Emboli and Embolic Load During Coronary Artery Bypass Grafting", *Ann Thorac Surg*; 63:1262–7 (1997).

Barbut et al., "Aortic Atheromatosis and Risks of Cerebral Embolization," *J Card & Vasc Anesth*; vol. 10, No. 1,: pp 24–30 (1996).

Barbut et al., "Aortic Atheroma is Related to Outcome but not Numbers of Emboli During Coronary Bypass," *Ann Thorac Surg*; 64:454–9 (1997).

(List continued on next page.)

*Primary Examiner*—Richard K. Seidel
*Assistant Examiner*—Kevin C. Sirmons
(74) *Attorney, Agent, or Firm*—Fulwider Patton Lee & Utecht, LLP

(57) ABSTRACT

The present invention includes an apparatus and methods for differentially perfusing a patient undergoing cardiopulmonary bypass. A cardiopulmonary bypass machine is configured to provide hypothermic oxygenated blood and normothermic oxygenated blood to an aortic balloon catheter. The catheter has arch perfusion ports and corporeal perfusion ports and is introduced into a patient's aorta and navigated transluminally until the occlusion balloon is located in the descending aorta. The occlusion balloon is inflated and hypothermic oxygenated blood is perfused to the arch vessels while normothermic oxygenated blood is perfused to the corporeal circulation. This procedure offers the benefit of cerebral protection from embolic events during cardiopulmonary bypass surgery.

26 Claims, 11 Drawing Sheets

U.S. PATENT DOCUMENTS

| | | | |
|---|---|---|---|
| 4,873,978 | 10/1989 | Ginsburg | 128/345 |
| 4,968,306 | 11/1990 | Huss et al. | 604/264 |
| 4,969,891 | 11/1990 | Gewertz | 606/200 |
| 5,059,205 | 10/1991 | El-Nounou et al. | 606/200 |
| 5,108,418 | 4/1992 | Lefebvre | 606/200 |
| 5,108,419 | 4/1992 | Reger et al. | 606/200 |
| 5,152,777 | 10/1992 | Goldberg et al. | 606/200 |
| 5,216,032 | 6/1993 | Manning | 514/718 |
| 5,242,451 * | 9/1993 | Harada et al. | 606/108 |
| 5,308,320 | 5/1994 | Safar et al. | 604/4 |
| 5,312,344 | 5/1994 | Grinfeld | 604/101 |
| 5,324,304 | 6/1994 | Rasmussen | 606/200 |
| 5,330,433 | 7/1994 | Fonger et al. | 604/164 |
| 5,334,142 | 8/1994 | Paradis | 604/53 |
| 5,354,288 | 10/1994 | Cosgrove | 604/264 |
| 5,368,555 | 11/1994 | Sussman et al. | |
| 5,375,612 | 12/1994 | Cottenceau et al. | 128/899 |
| 5,383,854 | 1/1995 | Safar et al. | 604/98 |
| 5,413,558 | 5/1995 | Paradis | 604/101 |
| 5,415,630 | 5/1995 | Gory | 604/53 |
| 5,425,724 | 6/1995 | Akins | 604/284 |
| 5,433,700 | 7/1995 | Peters | 604/4 |
| 5,437,633 | 8/1995 | Manning | 604/53 |
| 5,451,207 | 9/1995 | Yock | 604/53 |
| 5,458,574 | 10/1995 | Machold et al. | 604/101 |
| 5,478,309 | 12/1995 | Sweezer et al. | 604/4 |
| 5,496,277 | 3/1996 | Termin et al. | 604/104 |
| 5,522,834 | 6/1996 | Fonger et al. | 606/194 |
| 5,531,776 | 7/1996 | Ward et al. | 604/105 |
| 5,549,626 | 8/1996 | Miller | 606/200 |
| 5,584,803 | 12/1996 | Stevens et al. | 604/4 |
| 5,599,329 | 2/1997 | Gabbay | 604/284 |
| 5,611,338 * | 3/1997 | Gallup et al. | 128/634 |
| 5,616,137 | 4/1997 | Lindsay | 604/264 |
| 5,662,671 | 9/1997 | Barbut et al. | 606/170 |
| 5,678,570 | 10/1997 | Manning | 128/897 |
| 5,685,865 | 11/1997 | Cosgrove et al. | 604/239 |
| 5,695,457 | 12/1997 | St. Goar et al. | 604/4 |
| 5,697,905 | 12/1997 | d'Ambrosio | 604/96 |
| 5,702,368 | 12/1997 | Stevens et al. | 604/171 |
| 5,716,318 | 2/1998 | Manning | 600/16 |
| 5,725,496 | 3/1998 | Peters | 604/49 |
| 5,738,649 | 4/1998 | Macoviak | 604/43 |
| 5,738,652 | 4/1998 | Boyd et al. | 604/96 |
| 5,755,687 | 5/1998 | Donlon et al. | 604/53 |
| 5,755,784 | 5/1998 | Jarvik | 623/3 |
| 5,759,170 | 6/1998 | Peters | 604/4 |
| 5,766,151 | 6/1998 | Valley et al. | 604/96 |
| 5,769,812 | 6/1998 | Stevens et al. | 604/4 |
| 5,769,816 | 6/1998 | Barbut et al. | 604/96 |
| 5,769,828 | 6/1998 | Jonkman | 604/280 |
| 5,776,190 | 7/1998 | Jarvik | 623/3 |
| 5,792,094 | 8/1998 | Stevens et al. | 604/4 |
| 5,795,325 | 8/1998 | Valley et al. | 604/53 |
| 5,800,375 | 9/1998 | Sweezer et al. | 604/4 |
| 5,810,757 | 9/1998 | Sweezer et al. | 604/4 |
| 5,814,016 | 9/1998 | Valley et al. | 604/96 |
| 5,820,593 | 10/1998 | Safar et al. | 604/96 |
| 5,827,237 | 10/1998 | Macoviak et al. | 604/246 |
| 5,827,269 * | 10/1998 | Saadat | 606/28 |
| 5,833,671 | 11/1998 | Macoviak et al. | 604/247 |
| 5,843,031 * | 12/1998 | Hermann et al. | 604/95 |
| 5,846,260 | 12/1998 | Maahs | 606/200 |
| 5,863,366 * | 1/1999 | Snow | 156/143 |
| 5,906,588 | 5/1999 | Safar et al. | 604/64 |

OTHER PUBLICATIONS

Roach et al., "Adverse Cerebral Outcomes After Coronary Artery Bypass Surgery," *N Engl J Med*, vol. 335, No 25; pp. 1857–1863 (1996).

Aberg, "Signs of Brain Cell Injury During Open Heart Operations: Past and Present," *Ann Thorac Surg*; 59:1312–5 (1995).

Murkin, "The Role of CPB Management in Neurobehavioral Outcomes After Cardiac Surgery," *Ann Thorac Surg*; 59:1308–11 (1995).

Mills, "Risk Factors for Cerebral Injury and Cardiac Surgery," *Ann Thorac Surg* 1995, 59:1296–9.

Moody et al., "Brain Microemboli Associated with Cardiopulmonary Bypass: A Histologic and Magnetic Resonance Imaging Study," *Ann Thorac Surg*; 59:1304–7 (1995).

Murkin et al., "Statement of Consensus on Assessment of Neurobehavioral Outcomes After Cardiac Surgery," *Ann Thorac Surg*; 59:1289–95 (1995).

Sherman et al., "Heart–Brain Interactions: Neurocardiology Comes of Age," *Mayo Clin Proc*; 62:1158–1160 (1987).

van der Linden, "Cerebral Hemodynamics After Low–Flow Versus No–Flow Procedures," *Ann Thorac Surg*; 59:1321–5 (1995).

Newman et al., "Predictors of Cognitive Decline After Cardiac Operation," *Ann Thorac Surg*; 59:1326–30 (1995).

Venn et al., "Cardiopulmonary Bypass: Perioperative Cerebral Blood Flow and Postoperative Cognitive Deficit," *Ann Thorac Surg*; 59:1331–5 (1995).

Blauth, "Macroemboli and Microemboli During Cardiopulmonary Bypass," *Ann Thorac Surg*; 59:1300–3 (1995).

Sotaniemi, "Long–Term Neurologic Outcome After Cardiac Operation," *Ann Thorac Surg*; 59:1336–9 (1995).

Rogers AT, Neurological Effects of Cardiopulmonary Bypass; Cardiopulmonary Bypass Principles and Practice; Gravlee GP, 21:542.

Erath et al., "Balloon Catheter Occlusion of the Ascending Aorta," *Ann Thorac Surg*; 35:560–1 (1983).

Cosgrove DM, "Management of the Calcified Aorta: and Alternative Method of Occlusion," *Ann Thor Surg*; 36:718–719 (1983).

Baxter Research Medical, RMI Dispersion™ Aortic Cannula, Advertisement (1998).

3M™ Sarns™ Soft Flow Aortic Arch Cannula pp. 1–4, Advertisement (1994).

Research Medical™ Instructions for Use, RMI Aortic Arch Cannula Rev 5 (1994).

Braekken et al. "Cerebral Microembolic Signals During Caridopulmonary Bypass Surgery. Frequency, Time of Occurrence, and Association with Patient and Surgical Characteristics." *Stroke*; 1988–92. (1997).

Okiya et al. "Utilization of Triple Lumen Balloon Catheter for Occlusion of The Ascending Aorta During Distal Aortic Arch Surgery With Hypothermic Retrograde Cerebral Circulation Technique Through Left Thorocotomy." *J. Card Surg*; 10:699–702 (1995).

Rubenstein et al. "Percutaneous Aortic Balloon Occlusion." *Surg Gynecol Obstet*; 164:561–563 (1987).

Muehrcke et al. "Flow Characteristics of Aortic Cannulae." *J Card Surg*; 10:514–519 (1995).

Robicsek, "Administration of Hypothermic Cardioplegia in the Presence of Aortic Regurgitation." *Ann Thorac Surg.* Feb;39(2):192–3 (1985).

Technical Specifications Percluder® aortic occluding balloon, Datascope Corp. © 1987 Datascope Corp.

David P. Bichell, MD, et al., Axilloaxillary Cardiopulmonary Bypas: A Practical Alternative to Femorofemoral Bypass. ©1997 by The Society of Thoracic Surgeons Published by Elsevier Science Inc., pp. 702–705.

Joseph F. Sabik, MD, et al., Axillary Artery: An Alternative Site of Arterial Cannulation for Patients with Extensive Aortic and Peripheral Vascular Disease, ©1995 by Mosby–Year Book, Inc., The Journal of Thoracic and Cardiovascular Surgery, pp. 886–891.

Nicholas T. Kouchoukos, et al., Perfusion for Thoracic Aortic Surgery, Section V. Clinical Application and Management of CPB, pp. 636–654.

* cited by examiner

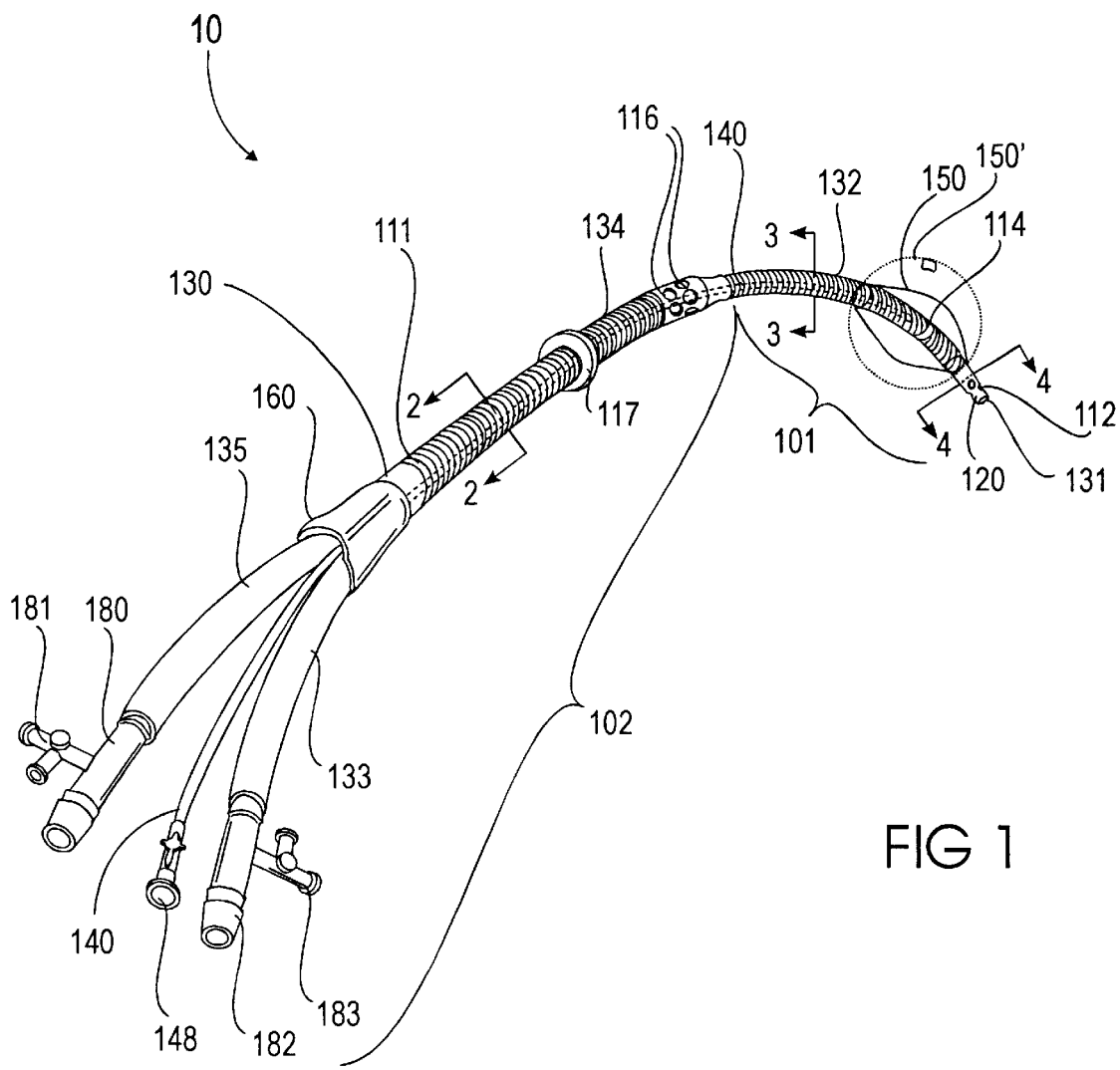
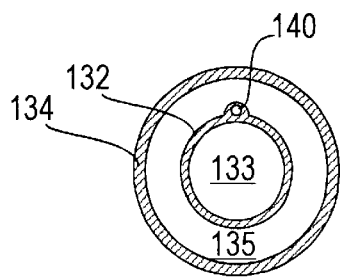
FIG 2
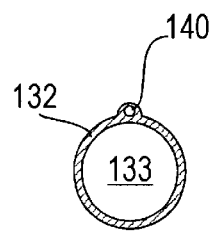
FIG 3
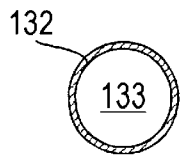
FIG 4
FIG 1

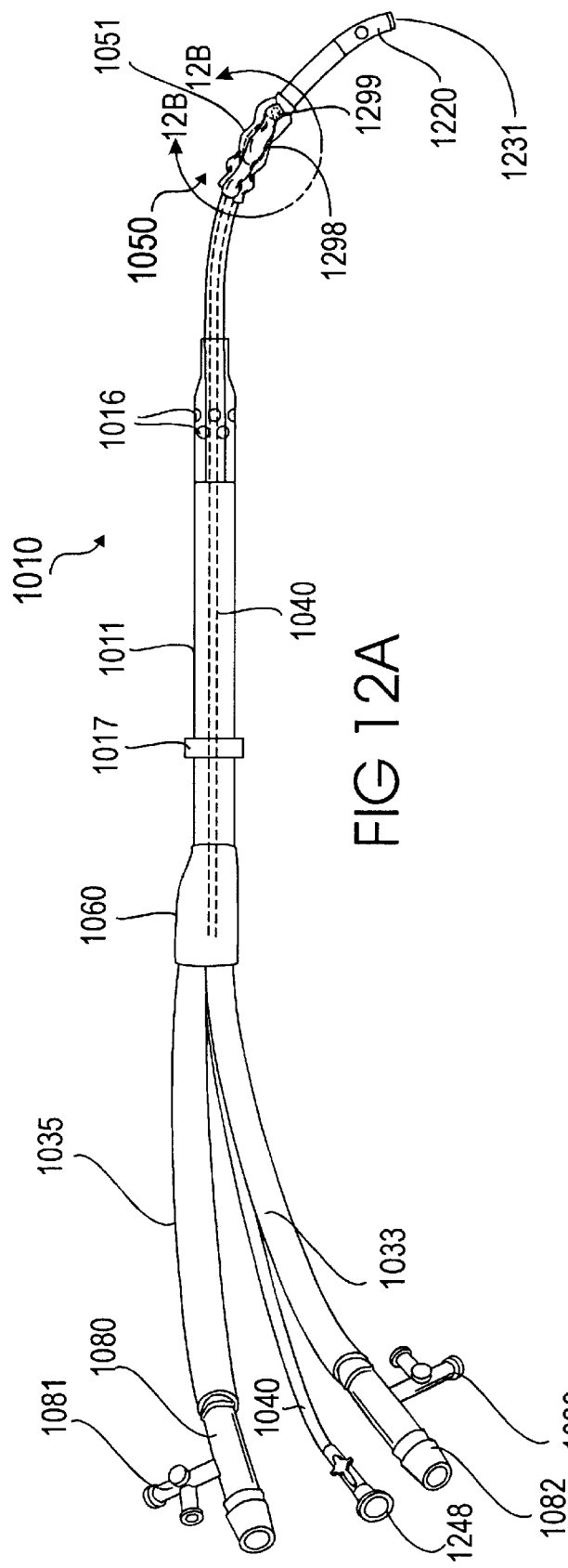
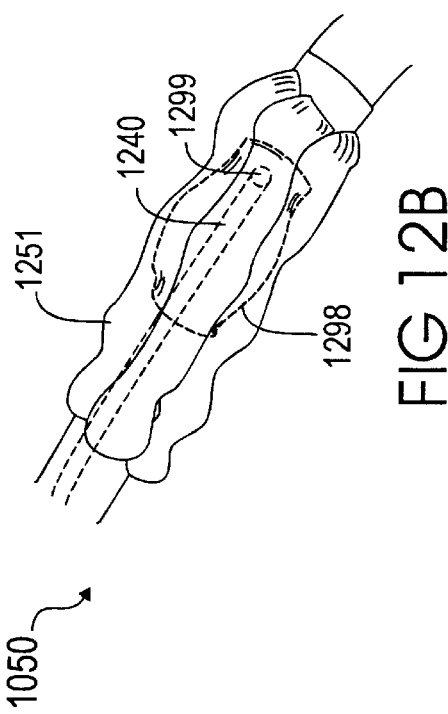
FIG 12A
FIG 12B

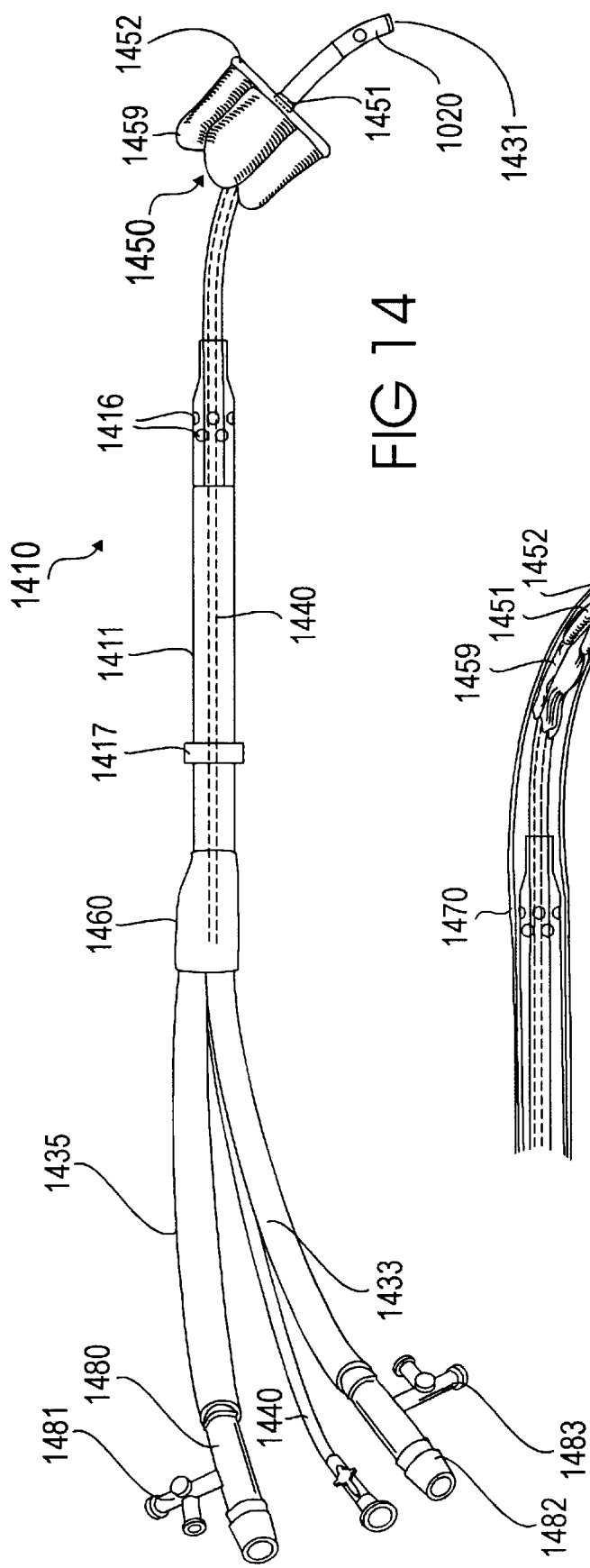
FIG 14
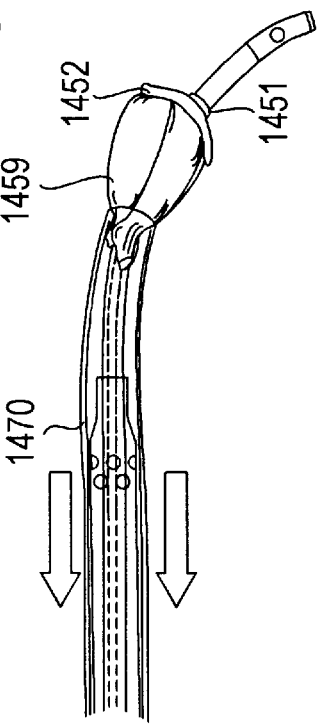
FIG 15
FIG 16

METHODS AND DEVICES FOR OCCLUDING A VESSEL AND PERFORMING DIFFERENTIAL PERFUSION

FIELD OF THE INVENTION

The present invention relates generally to medical devices and methods for performing cardiovascular, pulmonary and neurological procedures and more particularly to aortic catheter devices for cardiopulmonary bypass support of a patient during surgical interventions.

BACKGROUND OF THE INVENTION

Partial or full cardiopulmonary bypass (hereafter "CPB") support is needed for medical procedures requiring general anesthesia where lung function is to be arrested during routine and high-risk cardiovascular, cardioneural and other surgical interventions including beating, fully arrested or partially arrested cardiac procedures, to maintain cardiovascular, cardioneural and corporeal support of the respective heart, cerebral and corporeal organ systems. Such surgical interventions include treatment of aneurysms, congenital valve disease, and coronary artery disease. Cardiac interventions such as angioplasty, atherectomy, thrombectomy, coronary bypass grafting, and heart valve repair or replacement are some of the other procedures that can be performed.

In procedures where the heart is to be fully or partially arrested, it has been conventionally preferred that the heart and coronary vasculature be isolated from the rest of the cardiovascular system by application of an external cross clamp or side biting clamp. Isolation allows antegrade or retrograde perfusion of cold, warm or normothermic oxygenated blood cardioplegia or crystalloid cardioplegia to the coronary arteries to aid in the preservation of the myocardium and to prevent dispersion of cardioplegia to the rest of the body. The heart chambers may then be vented for decompression and to create a bloodless surgical field for intracardiac interventions. For rapid cooling and arrest of the myocardium in open-chest procedures, direct application of a topical ice slush or cold pericardial lavage into the thoracic space is performed simultaneously while the cold coronary perfusion process is being accomplished. While the heart is arrested, oxygenated blood is perfused to the rest of the body to maintain cerebral and corporeal support without perfusion to the coronary arteries, which could resuscitate the partially or fully arrested heart and obscure the surgical field with blood before completion of the surgical intervention.

A preferred way to accomplish CPB is by inserting a venous cannula into a venous blood vessel, typically the vena cava, withdrawing deoxygenated blood and directing the fluid to a connected pump. The pump circulates the withdrawn blood through a blood oxygenator, heat exchanger and filter apparatus and then perfuses the oxygenated and temperature controlled blood and other fluids through an aortic perfusion catheter inserted into the aorta of the patient.

Stroke and neurological deficit are well documented sequelae of the above cardiac surgery procedure. Recent literature has documented that the incidence of stroke is as high as 6.1% with an additional 30–79% of patients suffering from some form of cognitive deficit. Neurological deficit varies from patient to patient, however common injuries include: loss of memory, concentration, hand-eye coordination, and an increase in morbidity and mortality. The impact on the patient is significant, but factors such as age, the level of intellectual activity and the amount of physical activity pursued by the patient prior to surgery all affect the quality of life. Finally, patients who suffer from neurologic injury have a substantially prolonged hospital stay, with an attendant increase in cost (Neurological Effects of Cardiopulmonary Bypass; Rogers AT, Cardiopulmonary Bypass Principles and Practice; Gravlee GP, 21:542).

One of the likely causes of stroke and neurological deficit is the release of emboli into the blood stream during heart surgery. Potential embolic materials include atherosclerotic plaques or calcific plaques from within the aorta or cardiac valves and thrombus or clots from within the chambers of the heart. These potential emboli may be dislodged during surgical manipulation of the heart and the ascending aorta or due to high velocity jetting (sometimes called the "sandblasting effect") from the aortic perfusion cannula. In addition, application and release of an external cross clamp or side biting clamp has been shown to release emboli into the blood circulation. Other potential sources of emboli include gaseous microemboli formed when using a bubble oxygenator for CPB and "surgical air" that enters the heart chambers or the blood stream during surgery through open incisions or through the aortic perfusion cannula.

The following Journal articles addressing specific problems associated with emboli are listed below:
Journal Articles relating to Cerebral Embolization and Adverse Cerebral Outcomes After Cardiac Surgery: Determination or Size of Aortic Emboli and Embolic Load During Coronary Artery Bypass Grafting; Barbut et al.; Ann Thorac Surg 1997; 63:1262–7; Aortic Atheromatosis and Risks of Cerebral Embolization; Barbut et al.; J Card & Vasc Anesth, Vol 10, No 1, 1996: pp 24–30. Aortic Atheroma is Related to Outcome but not Numbers of Emboli During Coronary Bypass; Barbut et al.; Ann Thorac Surg 1997, 64:454–9; Adverse Cerebral Outcomes After Coronary Artery Bypass Surgery; Roach et al.; New England J of Med, Vol 335, No 25, 1996: pp. 1857–1863; Signs of Brain Cell Injury During Open Heart Operations: Past and Present; Åberg; Ann Thorac Surg 1995, 59:1312–5; The Role of CPB Management in Neuro behavioral Outcomes After Cardiac Surgery; Murkin; Ann Thorac Surg 1995,59:1308–11; Risk Factors for Cerebral Injury and Cardiac Surgery; Mills; Ann Thorac Surg 1995, 59:1296–9; Brain Microemboli Associated with Cardiopulmonary Bypass: A Histologic and Magnetic Resonance Imaging Study; Moody et al.; Ann Thorac Surg 1995, 59:1304–7; CNS Dysfunction After Cardiac Surgery: Defining the Problem; Murkin; Ann Thorac Surg 1995,59:1287; Statement of Consensus on Assessment of Neurobehavioral Outcomes After Cardiac Surgery; Murkin et al.; Ann Thorac Surg 1995, 59:1289–95; Heart-Brain Interactions: Neurocardiology Comes of Age; Sherman et al.; Mayo Clin Proc 62:1158–1160,1987; Cerebral Hemodynamics After Low-Flow Versus No-Flow Procedures; van der Linden; Ann Thorac Surg 1995, 59:1321–5; Predictors of Cognitive Decline After Cardiac Operation; Newman et al.; Ann Thorac Surg 1995,59:1326–30. Cardiopulmonary Bypass: Perioperative Cerebral Blood Flow and Postoperative Cognitive Deficit; Venn et al.; Ann Thorac Surg 1995, 59:1331–5; Long-Term Neurologic Outcome After Cardiac Operation; Sotaniemi; Ann Thorac Surg 1995, 59:1336–9; Macroemboli and Microemboli During Cardiopulmonary Bypass; Blauth; Ann Thorac Surg 1995, 59:1300–3.

Recently, there has been much development in the area of minimally invasive cardiac surgery (MICS) and the use of balloon catheters to address the clinical problems associated with a conventional median stemotomy and the attendant use of a cross clamp to occlude the ascending aorta. For example, U.S. Pat. No. Re 35,352 to Peters describes a single balloon catheter for occluding a patient's ascending aorta and a method for inducing cardioplegic arrest. A perfusion lumen or a contralateral arterial cannula is provided for supplying oxygenated blood during cardiopulmonary bypass. U.S. Pat. No. 5,584,803 to Stevens et al. describes a single balloon catheter for inducing cardioplegic arrest and a system for providing cardiopulmonary support during closed chest cardiac surgery. A coaxial arterial cannula is provided for supplying oxygenated blood during cardiopulmonary bypass. The occlusion balloon of these catheters must be very carefully placed in the ascending aorta between the coronary arteries and the brachiocephalic artery, therefore the position of the catheter must be continuously monitored to avoid complications.

In clinical use, these single balloon catheters have shown a tendency to migrate in the direction of the pressure gradient within the aorta. More specifically, during infusion of cardioplegia, the balloon catheter will tend to migrate downstream due to the higher pressure on the upstream side of the balloon and, when the CPB pump is on, the balloon catheter with tend to migrate upstream into the aortic root due to the higher pressure on the downstream side of the balloon. This migration can be problematic if the balloon migrates far enough to occlude the brachiocephalic artery on the downstream side or the coronary arteries on the upstream side.

Another important development in the area of aortic balloon catheters is the concept of selective aortic perfusion. Described in commonly owed U.S. Pat. Nos. 5,308,320, 5,383,854 and 5,820,593 by Peter Safar, S. William Stezoski, and Miroslav Klain is a double balloon catheter for segmenting a patient's aorta for selective perfusion of different organ systems within the body. Other U.S. patents which address the concept of selective aortic perfusion include; U.S. Pat. No. 5,738,649, by John A. Macoviak, U.S. Pat. Nos. 5,827,237 and 5,833,671 by John A.

Macoviak and Michael Ross; and commonly owned, copending patent application Ser. No. 08/665,635, filed Jun. 18, 1996, by John A. Macoviak and Michael Ross. All the above listed patents and patent applications, as well as all other patents referred to herein, are hereby incorporated by reference in their entirety.

Safar teaches the peripheral introduction of an aortic balloon catheter to establish CPB and to facilitate intravascular surgical interventions. Additionally, Safar teaches an apparatus and method of selective differential perfusion, which allows segmentation of the circulatory system into separate coronary, cerebral and corporeal subcirculations. The aortic balloon catheter allows establishment of CPB without the need for a thoracotomy, which may also facilitate minimally-invasive surgical procedures on the arrested heart. Although minimally invasive techniques provide a beneficial alternative to the open chest median sternotomy, the present invention specifically addresses a method where a thoracotomy, such as a median sternotomy, is desirable because of the need for direct exposure of the heart and an apparatus specifically designed for such a purpose.

U.S. Pat. No. 5,697,905 to d'Ambrosio teaches a single balloon, triple lumen catheter to be positioned in the ascending aorta to reduce the release of embolized air and particulate matter into general body circulation. The aforementioned device uses a suction lumen to remove released emboli.

The following U.S. patents relate to aortic filters associated with atherectomy devices in order to trap potential emboli before they are introduced into the general circulation: U.S. Pat. Nos. 5,662,671 and 5,769,816. The following international patent applications also relate to aortic filters and aortic filters associated with atherectomy devices: WO 97/17100, WO 97/42879, WO 98/02084.

Catheters intended to occlude the descending aorta are disclosed by Manning, U.S. Pat. Nos. 5,678,570, 5,216,032, and Paradis, U.S. Pat. No. 5,334,142. However, none of the aforementioned devices were designed, nor intended, for use in the manner of the present invention.

The previous inventions do not adequately address the patient population where a conventional median sternotomy and differential perfusion are desirable. Therefore, what has been needed and previously unavailable is an apparatus and system to selectively and differentially perfuse the cerebral sub-circulation with hypothermic oxygenated blood and perfuse the corporeal sub-circulation with normothermic oxygenated blood. The present invention solves this immediate problem, as well as others.

SUMMARY OF THE INVENTION

In keeping with the foregoing discussion, it is a primary object of the present invention to provide a method and apparatus which is as familiar to physicians as possible, while at the same time introducing the concept of differential perfusion when a thoracotomy, such as a median sternotomy is implemented. Differential perfusion will enable the clinician to specifically determine flow, temperature and composition of perfusate delivered to the brain differentially from the body. Isolation of the cerebral circulation from the corporeal circulation facilitates the creation of a neuroprotective environment through temperature and chemical control, allowing the brain to be cooled to a significantly lower temperature than the body. Lowering the temperature of the brain results in a corresponding reduction of blood flow to the brain since the metabolic demands of the tissue for oxygen are reduced. This benefit allows for an overall reduction in flow, volume and cycles of blood to the brain and less opportunity for emboli to be introduced into the cerebral blood circulation during surgical interventions.

In addition, prolonged hypothermia for the brain while the body is warm extends the neuroprotective period while avoiding issues associated with systemic hypothermia, such as coagulopathy, low cardiac output and prolonged Intensive Care Unit time. Furthermore, by keeping the heart relatively normothermic, the problem of cardiac arrythmias associated with hypothermia is better controlled.

The invention contemplates the use of a cardiopulmonary bypass machine configured with two heat exchangers coupled to an aortic catheter with a flow control regulator mounted on the catheter shaft to at least partially occlude the descending aorta, while a standard cross clamp occludes the ascending aorta. The aortic catheter and flow control regulator used in concert will create a segmentation of the aorta allowing for differential perfusion of the arch circulation separate from the corporeal circulation. The heart is kept in an arrested state through hypothermia, hypothermic perfusion, or by injecting crystalloid cardioplegia, blood cardioplegia or any combination thereof into the coronary arteries of the heart.

The differential perfusion system of the present invention includes a catheter with an elongated catheter shaft, an arch perfusion lumen connected to an arch perfusion port, a corporeal perfusion lumen connected to a corporeal perfusion port, and a flow control regulator positioned between the two ports. The shaft has a proximal portion that is composed of the corporeal lumen and the arch lumen extending in a coaxial relationship. The arch perfusion lumen terminates at a point along the catheter shaft and the corporeal lumen continues through the distal portion of the catheter shaft, terminating at the distal opening of the catheter shaft. The distal corporeal perfusion port, defined by the distal opening and accompanying corporeal ports, is in fluid communication with a proximal fitting that is connected to a cardiopulmonary bypass machine. The distal corporeal perfusion port is sized and dimensioned to provide optimal flow and pressure to the corporeal sub-circulation while minimizing the undesirable "sandblasting effect".

The internal arch perfusion lumen extends part way through the catheter shaft and terminates at a distal arch perfusion port. The proximal fitting of the arch perfusion lumen is connected to a cardiopulmonary bypass machine. The distal port is sized and dimensioned to provide optimal flow and pressure to the cerebral sub-circulation.

A flow control regulator is located on the distal portion of the catheter shaft and resides between the corporeal perfusion port and the arch perfusion port. The flow control regulator may be in the form of an inflatable balloon or a selectively deployable valve. The design feature of having coaxial lumens allows for a smaller diameter distal portion and a smooth transition in diameter without sacrificing a consistent internal diameter for corporeal flow. Alternatively, the distal portion could remain the same size as the proximal portion, allowing for a larger internal diameter in the distal portion for corporeal flow.

In use, the surgeon will typically place a purse string suture and aortotomy after which, the catheter tip is inserted into the ascending aorta. The distal tip of the catheter may be adapted to be used in conjunction with an internal stylet or trocar or may be preoperatively prepared in a cold saline solution to create a more rigid tip that becomes soft and flexible after insertion, thereby eliminating the need for a stylet or trocar.

Once inserted, the distal tip is advanced transluminally in an antegrade direction through the vessel until the flow control regulator, is positioned in the descending aorta downstream of the left subclavian artery. Placement may be verified in a number of ways well known in the art such as transesophageal echography (TEE), X-ray fluoroscope or fiberoptic illumination. However, since the intraluminal distance to be covered is relatively short, 4–8 inches to travel downstream of the left subclavian artery after insertion, proper placement is easily verified by determining the amount of catheter shaft located within the vessel by reference to a suture ring located external to the catheter shaft. Furthermore, once the flow control regulator is placed in the proper position there is little concern that displacement will occur since the catheter shaft is rigid enough to resist undesired movement yet compliant enough to move through the vessel without damaging the interior vessel wall.

After proper placement is verified, the surgeon generally begins CPB and starts perfusing the aorta prior to application of an external cross-clamp or internal cross-clamp to the ascending aorta. Once minimum proper perfusion flow has been established the surgeon will apply the cross-clamp to the aorta or inflate an occlusion balloon inside the aorta and supply crystalloid cardioplegia or blood cardioplegia to the myocardium to completely or partially arrest the heart. The flow control regulator is then activated, at least partially occluding the descending aorta downstream of the left subclavian artery, thereby creating a compartmentalization of the aorta. Upstream of the flow control regulator, hypothermic oxygenated blood is perfused to the arch vessels through the arch perfusion port. Downstream of the flow control regulator, normothermic oxygenated blood is perfused to the corporeal circulation through the corporeal perfusion port. For a description of a CPB machine that is specially configured with multiple heat exchangers and multiple pump heads to provide oxygenated blood to an aortic catheter with different temperatures, reference is made to commonly owned copending application Ser. No. 60/084, 835 filed on Dec. 4, 1998, which is hereby incorporated by reference in its entirety. Upstream of the cross-clamp, antegrade or retrograde cardioplegia is supplied keeping the heart in a partially or completely arrested state.

BRIEF DESCRIPTION OF THE DRAWINGS

FIG. 1 shows a perspective view of a first embodiment of the aortic catheter of the present invention configured for antegrade deployment via the ascending aorta.

FIG. 2 is a magnified lateral cross section of the aortic catheter of FIG. 1 taken along the line 2—2 in FIG. 1.

FIG. 3 is a magnified lateral cross section of the aortic catheter of FIG. 1 taken along the line 3'3 in FIG. 1.

FIG. 4 is a magnified lateral cross section of the aortic catheter of FIG. 1 taken along the line 4—4 in FIG. 1.

FIGS. 11 and 12 illustrate a fifth embodiment of the aortic catheter of the present invention with an actively deployable peripheral flow control valve regulator that is actuated through an inflatable actuating balloon.

FIGS. 14 through 16 illustrate a seventh embodiment of the aortic catheter of the present invention wherein the central flow control valve regulator is actively deployed by using a second catheter.

DETAILED DESCRIPTION OF THE INVENTION

Figure 5:
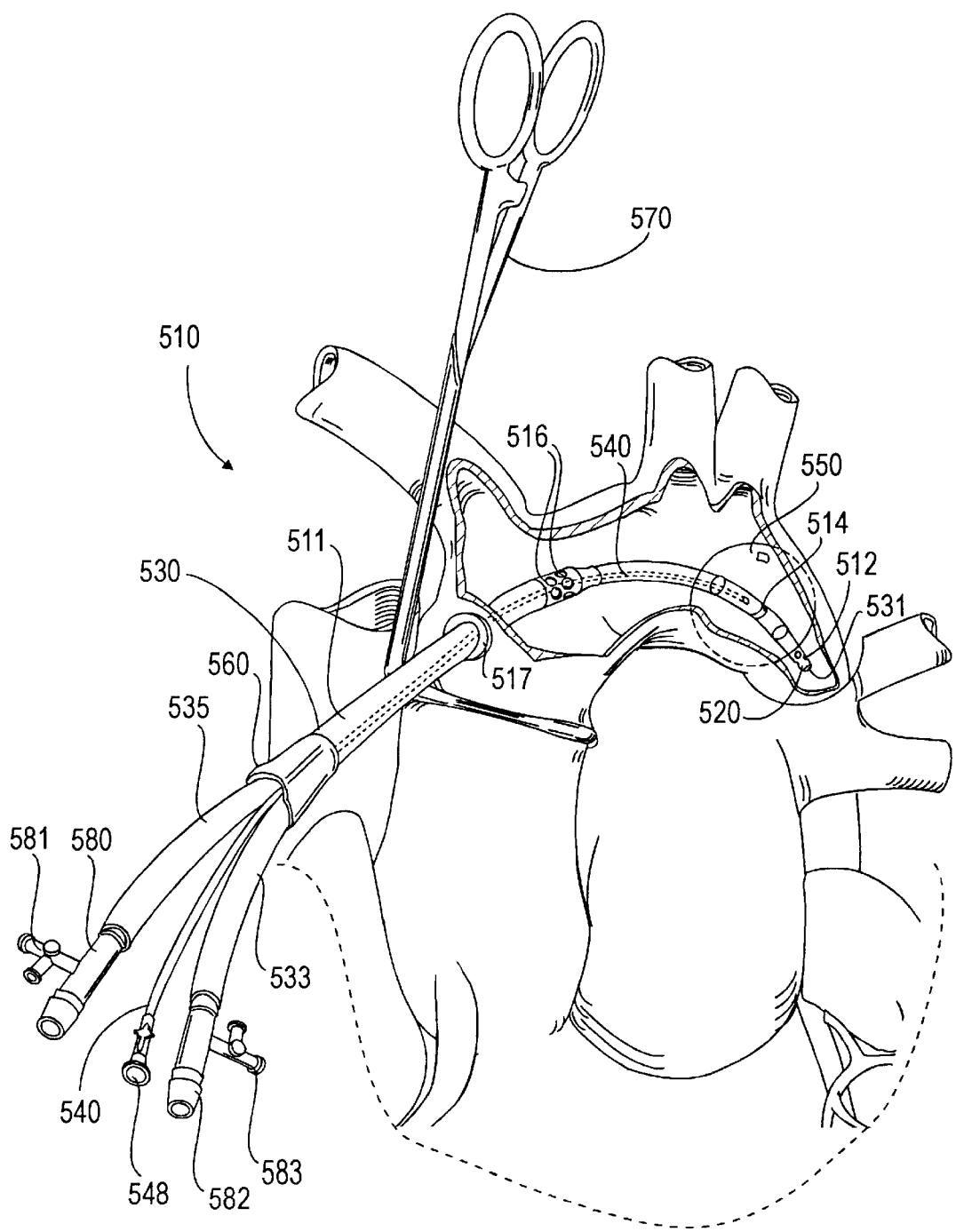
FIG. 5 is a schematic diagram showing the aortic catheter of FIG. 1 deployed within a patient's aorta.

FIGS. 1 through 3 illustrate a first embodiment of the aortic catheter 10 of the present invention, which is configured for antegrade deployment via the ascending aorta. FIG. 1 is a perspective view of the shaft portion of the aortic catheter 110. FIG. 2 is a magnified lateral cross section of the aortic catheter 110 taken along the line 2—2 in FIG. 1. FIG. 3 is a magnified lateral cross section of the aortic catheter 110 taken along the line 3—3 in FIG. 1.

Referring to FIG. 1 the aortic catheter 110 has an elongated shaft 111 with a proximal end 130 and a distal end 131. The elongated catheter shaft 111 should be long enough to be inserted into the ascending aorta and guided transluminally in an antegrade direction such that the distal tip 120 and the flow control regulator 150 are positioned in the descending aorta. With the aforementioned requirements in mind, the overall length of the catheter shaft 111 is preferably between 4 and 30 cm, more preferably between 7 and 20 cm, most preferably between 12 and 15 cm.

The aortic catheter 110 is preferably configured to provide differential flow, pressure, temperature and chemical composition. Although differential flow and pressure can be accomplished with a single blood flow lumen, by adding another lumen, either in a side-by-side arrangement or in a coaxial relationship, differential flow, temperature and chemical composition can be accomplished. In one embodiment, as exemplified in FIG. 1, the elongated shaft 111 has a proximal coaxial portion 102 and a distal portion 101. As shown in FIG. 2, which is a magnified lateral cross-section of the aortic catheter 110 of FIG. 1 taken along the line 2—2, the proximal coaxial portion 102 has three lumens: a corporeal perfusion lumen 133, an arch perfusion lumen 135 and a flow control regulator lumen 140.

In a particularly preferred embodiment, the proximal portion 102 may be further described as having an inner coil reinforced shaft 132 and an outer 134 coil reinforced shaft configured in a co-axial relationship. The coil reinforced catheter shafts 132 and 134 may be made from any number of materials such as polymers and elastomers, which include, but are not limited to, polyvinylchloride, polyurethane, polyethylene, polypropylene, polyamides (nylons), polyesters, latex, silicone, and alloys, copolymers and reinforced composites thereof. In addition, the coil reinforcement may be achieved by embedding, laminating, or coextruding flat wire, helically wound wire or braided wire on or into the shaft material. The inner coil reinforced shaft 132 and the outer coil reinforced shaft 134 are arranged in a coaxial relationship such that an annular space is created therebetween defining the arch perfusion lumen 135. The corporeal perfusion lumen 133 is defined by the internal diameter of the inner coil reinforced shaft 132. The proximal coaxial portion 102 of the shaft 111 terminates at one or more arch perfusion ports 116 in an unreinforced area along the length of the catheter shaft 111 proximal to the flow control regulator 150. Alternatively, the arch perfusion ports 116 may be located in a coil reinforced area of the catheter shaft 111. The termination position may vary, however arch anatomy is a primary consideration and the arch perfusion ports 116 are intended to be located near the arch vessels to enable optimum perfusion. The arch perfusion ports are sized and configured to provide optimal flow with a low peak velocity to limit the "sandblasting" effect in the aorta. In an exemplary embodiment there are 8 arch perfusion ports 116 residing around the exterior of the catheter shaft 111. Alternatively, there may be more or less perfusion ports depending upon lumen size and kink resistance in the aortic shaft.

As shown in FIG. 3, which is a magnified lateral cross section of the aortic catheter of FIG. 1 taken along line 3—3, the corporeal perfusion lumen 133 and the flow control regulator lumen 140 continue distally to form the distal portion 101 of the catheter shaft 111. The distal portion 101 of the catheter shaft 111 preferably has a length of 2–10 cm, more preferably 3–8 cm, most preferably 4–6 cm. The coaxial design allows for a smaller diameter distal portion 101, relative to the diameter of the proximal portion 102. Alternatively, the diameter of the distal portion 101 can be increased to allow for a larger perfusion lumen 33 without creating an overall increase in the diameter of the catheter 110. In either case, optimal corporeal flow can be accomplished through the perfusion lumen 133. Preferably, the catheter shaft 111 has an outer diameter that is from approximately 9 to 22 French (3.0–7.3 mm diameter), more preferably from approximately 12 to 18 French (4.0–6.0 mm diameter). Preferably, the distal portion 101 of the elongated catheter shaft 111 has a preformed 90-degree curvature specially designed to conform to the patient's aortic anatomy.

As shown in FIG. 4, which is a magnified lateral cross section of the aortic catheter of FIG. 1 taken along line 4—4, the corporeal perfusion lumen 133 terminates at the distal opening 112 of the elongated catheter shaft 111 as well as one or more corporeal perfusion ports 112 residing in the exterior of the insertion tip 120. The corporeal perfusion ports 112 are sized and configured to perfuse blood at an optimal flow with a low peak velocity. The corporeal perfusion ports 112 surround the insertion tip 120 to ensure proper perfusion and even distribution of perfusates. In an exemplary embodiment, the number of corporeal perfusion ports 112 is 5, including the distal opening. Alternatively, there may be more or less corporeal perfusion ports 112 depending upon the material construction of insertion tip 120 and the size of the corporeal lumen 133. The corporeal perfusion ports may reside in an unreinforced portion of the aortic catheter shaft 111 or in a reinforced portion of the aortic catheter shaft 111.

The coaxial relationship between the two shafts creates an annular space that represents the arch perfusion lumen 135. The inner coil reinforced shaft 132 has an internal diameter that is preferably between 0.025" and 0.300", more preferably between 0.100" and 0.225", most preferably between 0.140" and 0.185". The outer coil reinforced shaft 134 has an internal diameter preferably between 0.150" and 0.350", more preferably between 0.200" and 0.325", most preferably between 0.225" and 0.300".

The arch perfusion lumen 35 is preferably configured to provide a flow rate of 0.1 L/min to 3 L/min with a pressure drop between 0 mm Hg and 300 mm Hg, more preferably configured to provide 0.25 L/min to 2.5 L/min with a pressure drop between 0 mm Hg and 200 mm Hg, most preferably configured to provide 1 L/min to 2 L/min with a pressure drop between 0 mm Hg and 100 mm Hg.

The corporeal lumen 33 is preferably configured to provide a flow rate of 0.5 L/min to 8 L/min with a pressure drop between 0 mm Hg and 300 mm Hg, more preferably configured to provide 2 L/min to 6 L/min with a pressure drop between 0 mm Hg and 200 mm Hg, most preferably configured to provide 3.00 L/min to 5.00 L/min with a pressure drop between 0 mm Hg and 100 mm Hg.

The combined flow rate of the arch and corporeal perfusion lumens is preferably between 0.5 L/min and 10 L/min with a pressure drop between 0 mm Hg and 300 mm Hg, more preferably the flow rate is between 1 L/min and 9 L/min with a pressure drop between 0 mm Hg and 200 mm Hg, most preferably the flow rate is between 2 L/min and 8 L/min with a pressure drop between 0 mm Hg and 100 mm Hg.

A flow control regulator 150 is located on the distal portion 101 of the catheter shaft 111 and is actuated through the actuation lumen 140 once proper placement in the descending aorta has been established. The flow control regulator 150 is designed to prohibit substantial fluid flow in the aorta however, direct engagement with the vessel wall may not always be necessary to accomplish desired results. Nevertheless, when engagement with the vessel wall does occur it is non-traumatic.

The flow control regulator 150 in this particular embodiment is in the form of an expandable occlusion balloon, actuated through an inflation lumen 140. The balloon is attached to the catheter shaft 111 by any number of known methods such as heat welding or adhesive bonding, for example ultraviolet activated adhesive. Suitable materials for the flow control regulator 150 include flexible polymers and elastomers, which include, but are not limited to, polyvinylchloride, polyurethane, polyethylene, polypropylene, polyamides (nylons), polyesters, latex, silicone, and alloys, copolymers and reinforced composites thereof Manufacturing techniques for making the balloons include dipping and or blow molding.

The inflatable flow control regulator 150 has a deflated state, in which the diameter is preferably not much larger than the diameter of the catheter shaft 111, and an inflated state, in which the flow control regulator 150 expands to a diameter sufficient to prohibit substantial blood flow in the descending aorta of the patient. For use in adult human patients, the flow control regulator 150 preferably has an inflated outer diameter of approximately 1.5 cm to 4.0 cm. Preferably, the flow control regulator 150 has an inflated length that is not significantly longer than its inflated diameter, or, more preferably, is shorter than its inflated diameter.

The aortic catheter 110 may include one or more markers, in the form of radiopaque markers and/or sonoreflective markers, to enhance imaging of the aortic catheter 110 using fluoroscopy or ultrasound, such as transesophageal echography (TEE). In this illustrative embodiment, the aortic catheter 110 includes a distal radiopaque marker 114 positioned within the flow control regulator 150. The radiopaque marker may be made of a ring of dense radiopaque metal, such as gold, platinum, tantalum, tungsten or alloys thereof, or a ring of a polymer or adhesive material heavily loaded with a radiopaque filler material.

The distal tip 120 is made from any number of known materials such as polymers and elastomers, which include, but are not limited to, polyvinylchloride, polyurethane, polyethylene, polypropylene, polyamides (nylons), polyesters, latex, silicone, and alloys, copolymers and reinforced composites thereof. In addition, the distal tip may be made from a temperature sensitive material having transition temperatures wherein at 0 degrees Celsius the material is extremely hard, at 25 degrees Celsius the material is of sufficient rigidity to be inserted into a vessel a traumatically and at 35 degrees Celsius the material is very flexible and non-traumatic. A method of achieving the above-described results is to place the temperature sensitive tip in a 4 degree saline solution preoperatively to be inserted at the appropriate time during the surgical procedure. In one illustrative embodiment the tip is made from a temperature sensitive polyurethane such as TECOFLEX or TECOPHILIC. Alternatively, the distal tip may be made of the same material as the catheter shaft 111, or of a soft material for atraumatic introduction into the aorta. The distal tip 120 may have multiple corporeal flow ports 112 to reduce the "sandblasting" effect when oxygenated blood is infused through the corporeal perfusion lumen 133 or alternatively may have a single opening with a blood diffuser (not shown).

FIG. 5 is a schematic diagram showing an aortic catheter 510 according to the present invention deployed within a patient's aorta. Mounted to the proximal end 530 of the catheter shaft 511 is a manifold 560 with fittings for each of the catheter lumens. The arch perfusion lumen 535 is connected to a ¼ inch barb connector 580 for coupling to a perfusion pump or the like and a luer connector 581, which may be used for monitoring perfusion pressure, for withdrawing fluid samples or for injecting medications or other fluids. The balloon inflation lumen 540 is connected to a luer connector 548 or other fitting suitable for connection to a syringe or balloon inflation device. The corporeal perfusion lumen 533 is connected to a ⅜ inch to ¼ inch barb reducer 582 for connection to a perfusion pump, and attached to the barb reducer 582 is a luer connector 583.

A thorocotomy, such as a median stemotomy, is performed creating direct visualization of the heart and aorta, followed by the placement of a purse string suture and an aortotomy incision inside the purse string on the surface of the ascending aorta. If an optional temperature sensitive tip is used, the catheter 510 may be preoperatively placed in a 4 degree centigrade saline solution to create a more rigid distal tip 120 suitable for insertion through the aortotomy incision. During this procedure or prior thereto, the venous drainage circuit is prepared by cannulating either the vena cava and or the right atrium. Cannulation can be accomplished with either a "two stage" venous cannula, a single stage venous cannula or by separate venous cannulation of the superior and inferior vena cava though the right atrium.

The aortic catheter 510 is advanced until the flow control regulator 550 is positioned downstream of the left subclavian artery. Evidence of proper position is easily established by pre-positioning the suture ring 517 on the catheter shaft 511 such that, when the suture ring touches the vessel surface proper, position of the flow control regular 550 downstream of the left subclavian has been completed.

Using a multihead cardiopulmonary bypass pump or the like, oxygenated blood is pumped through the corporeal 535 and arch 533 perfusion lumens and out the corresponding corporeal perfusion ports 512 and the arch perfusion ports 516 to take some of the pumping load off of the heart. The flow control regulator 550 is inflated and an aortic cross clamp 570 is applied, effectively partitioning the aorta. Thereafter, a cardioplegic agent, such cold crystalloid cardioplegia or blood cardioplegia, is infused through a separate cardioplegia needle or catheter placed in the aortic root upstream of the cross clamp 570 to induce cardioplegic arrest. Normothermic perfusion is maintained through the corporeal perfusion ports 512 and hypothermic perfusion is maintained through the arch perfusion ports 516. Arrest of the heart is maintained by infusing the cardioplegic agent through a cardioplegia needle, an antegrade infusion catheter or by retrograde infusion through a coronary sinus catheter as long as necessary for completion of the surgical procedure.

Perfusion temperatures, perfusate compositions and flow rates may be optimized to each of the segmented regions of the patient's circulation for optimal organ preservation while on cardiopulmonary bypass. While the aortic catheter 510 is deployed the rigid yet flexible coil reinforced shaft 11 stabilizes and anchors the flow control regulator 550 preventing upstream or downstream migration of the flow control regulator 550 due to differential pressures within the aorta. The pressure differential on the flow control regulator 550 also helps to place the shaft 511 in tension, further helping to prevent migration of the flow control regulator. At the completion of the surgical procedure, the external cross clamp is removed to allow oxygenated blood to flow into the patient's coronary arteries, whereupon the heart should resume normal sinus rhythm after the affects of the cardioplegia have sufficiently dissipated. If necessary, cardioversion or defibrillation shocks may be applied to restart the heart. The patient is then weaned off of bypass and the aortic catheter 510 and any other cannulae are withdrawn.

Figure 6:
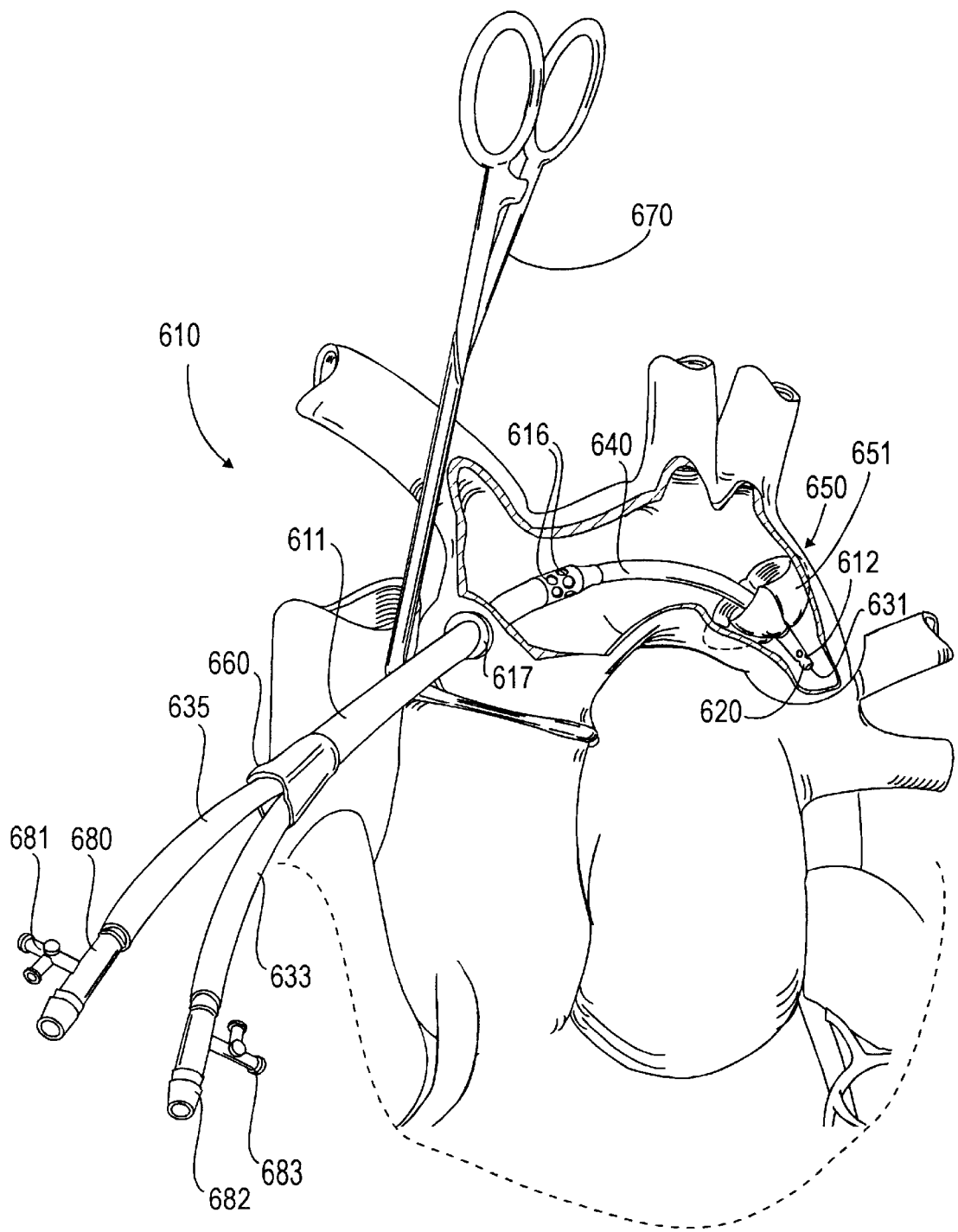
FIG. 6 is a schematic diagram showing a second embodiment of the aortic catheter of the present invention with a passively activated peripheral flow control valve regulator.

FIG. 6 is a schematic diagram showing a second embodiment of the aortic catheter 610 with a flow control regulator 650 in the form of a peripheral flow control valve regulator 650. In this exemplary embodiment, the peripheral flow control valve regulator 650 would preferably be in the form of a retrograde, peripheral flow valve, as described in commonly owned, U.S. Pat. Nos. 5,827,237, 5,833,671 and commonly owned, copending application Ser. No. 08/664,360, which have previously been incorporated by reference. The peripheral flow control valve regulator 650 is constructed with one or more valve leaflets 651 pivotally attached to the catheter shaft 611.

The peripheral flow control valve regulator 650 may be passively deployed in response to positive perfusion pressure in the aortic arch downstream of the cross clamp 670. This pressure passively activates the leaflets 651 by pivoting them outward to seal against the wall of the descending aorta. Alternatively, passive deployment may be accomplished by manufacturing the peripheral flow control valve regulator 650 of biocompatible materials having elastic shape memory that urges the valve leaflets 651 to pivot outward toward the vessel wall.

Figure 7:
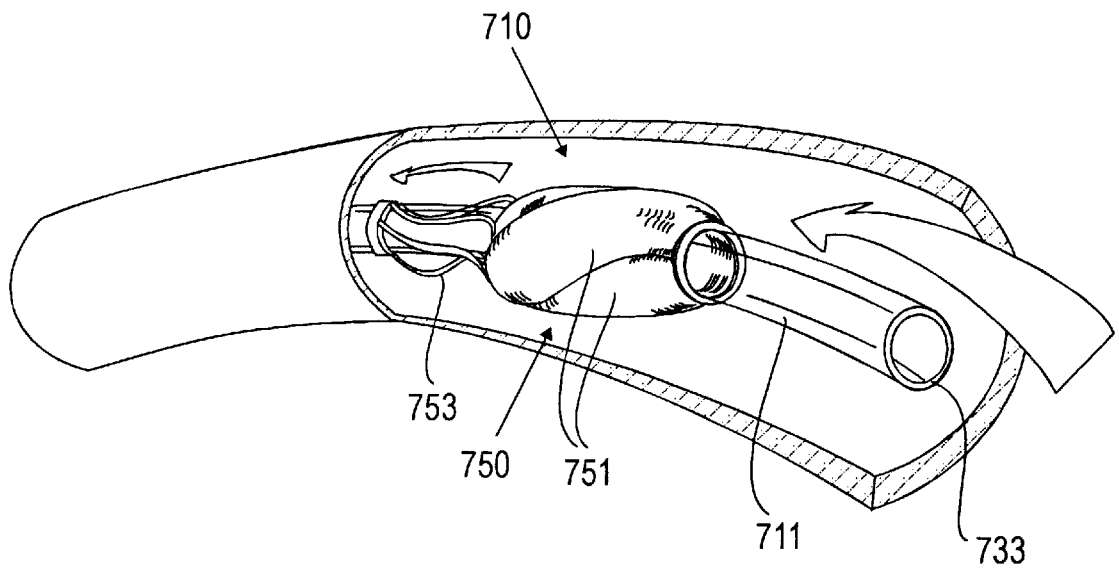
FIGS. 7 and 8 illustrate a third embodiment of the aortic catheter of the present invention with an actively deployable peripheral flow control valve regulator and attached actuation wires.
Figure 8:
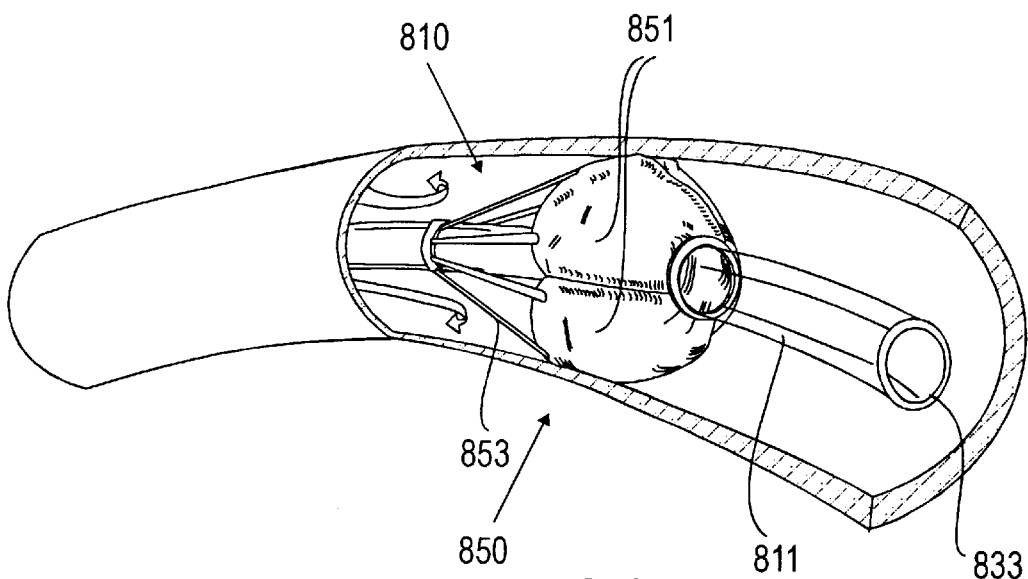

In place of or in addition to the passive valve deployment, the valve may be actively deployed. FIGS. 7 and 8 illustrate a third embodiment of the present invention where the peripheral flow control valve regulator 850 is actively deployed by one or more actuation wires 853 extending through, on top, inside or in a separate lumen of the elongated catheter shaft 811 and attached to the valve leaflets 851. FIG. 7 depicts the peripheral flow control valve regulator 750 in the undeployed state wherein the valve leaflets have a low profile and wrap around the catheter shaft 711 creating a smooth outer surface. This low profile is especially beneficial when inserting and removing the catheter from the ascending aorta in order to prevent excessive trauma to the exterior and interior of the vessel wall. FIG. 8 depicts the peripheral flow control valve regulator 850 in the deployed state wherein the valve leaflets 851 are actuated outward from the catheter shaft 811 through the attached actuation wires 853. The actuation wires 853 may be within the catheter shaft, on the outside of the catheter shaft or have their own separate actuating lumens. In any embodiment, the actuation wires 853 actuate the valve leaflets outward toward the vessel wall.

Figure 9:
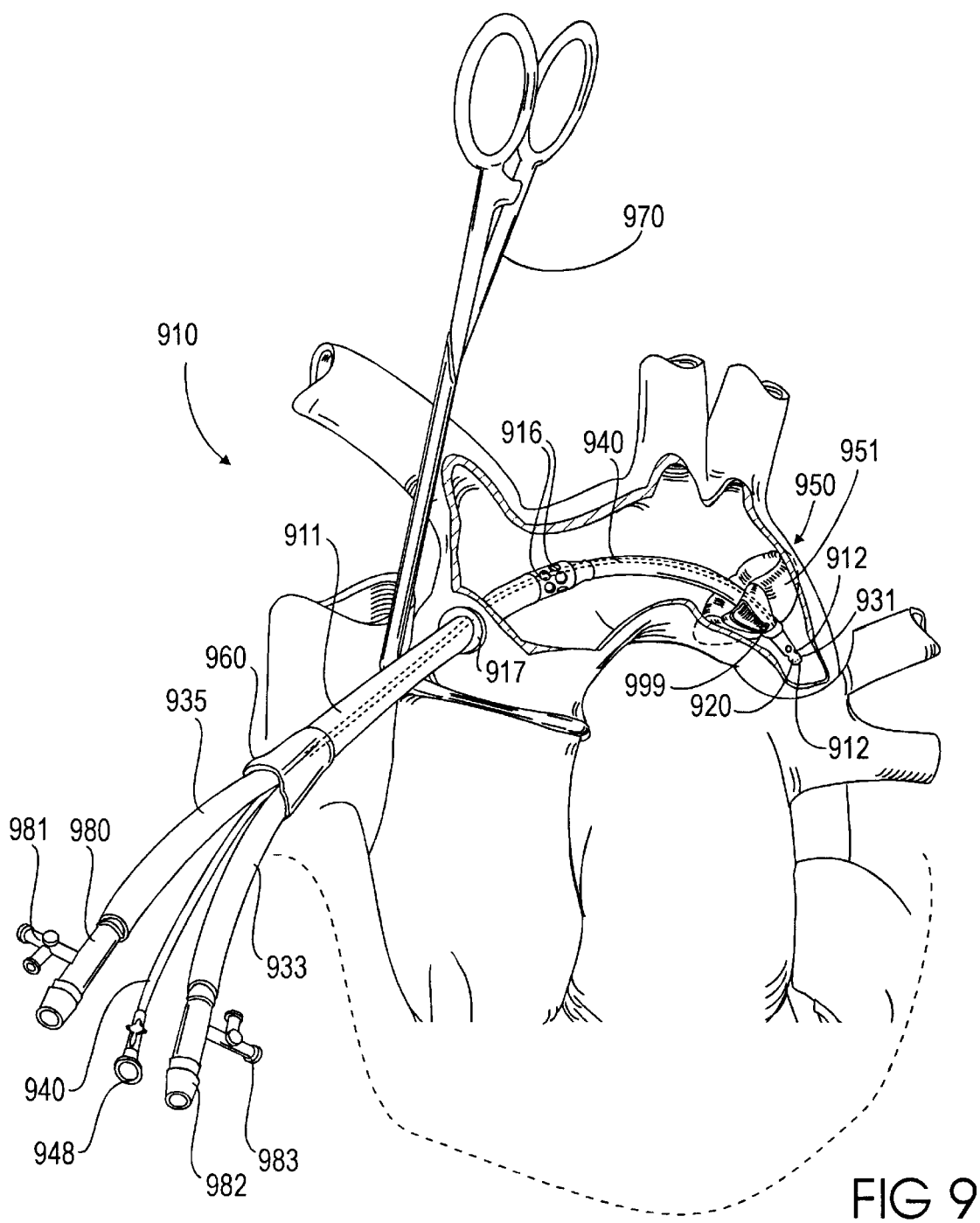
FIGS. 9 and 10 illustrate a fourth embodiment of the aortic catheter of the present invention with an actively deployable peripheral flow control valve regulator that is inflatable through an inflation lumen.
Figure 10:
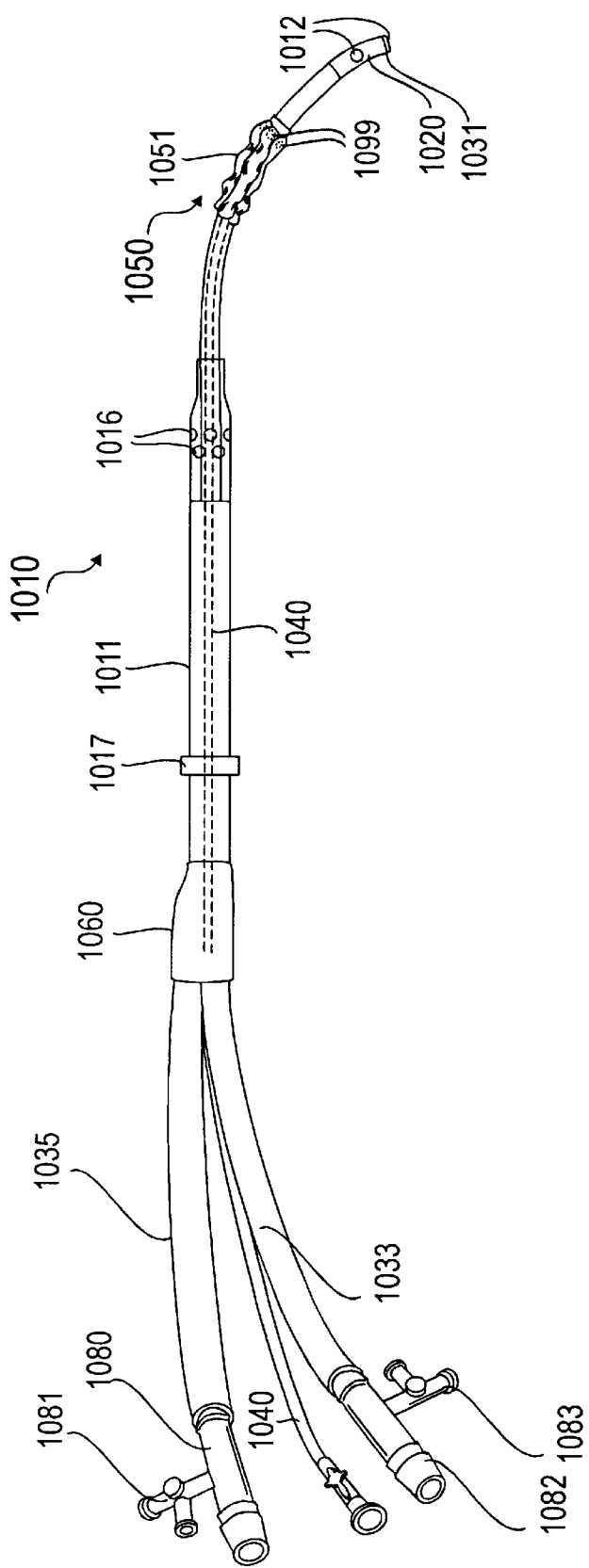

FIG. 9 illustrates a fourth embodiment of the present invention where the peripheral flow control valve regulator 950 is actively deployed using an inflation lumen 940 extending through the elongated catheter shaft 911 and terminating at an inflation port 999 within the valve leaflets 951. In this illustrative embodiment, the valve leaflets 951 are formed using heat bonding or adhesives to create triangular shaped leaflets configured in an overall funnel shape, where the valve leaflets 951 are configured to be inflated through a single inflation port 999. Alternatively, the valve leaflets 951 may be independent of one another and separately inflatable through an inflation port 999. Where the leaflets 951 are independent and separately inflatable, their inflated shape is triangular in configuration wherein the apex of the triangle is attached to the catheter shaft 911. Inflation of the valve leaflets 951 tends to pivot the leaflets outward toward the vessel wall. For maximum occluding, all the valve leaflets 951 are inflated creating an overlapping leaflet arrangement resulting in a complete funnel or umbrella configuration. Alternative shapes, such as squares, rectangles trapezoids or circles may be used to form the valve leaflets 951, since a variety of shapes are capable of creating an overall occluding mechanism. Inflation of the valve leaflets 951 may be accomplished by using a syringe or power injector connected to the inflation lumen 940 to hydraulically inflate the valve leaflets 951 with saline, water, blood, contrast or any combination thereof FIG. 10 depicts the peripheral flow control valve regulator 1050 of FIG. 9 in the undeployed state wherein the valve leaflets have a low profile and wrap around the catheter shaft 1011 creating a smooth outer surface. This low profile is especially beneficial when inserting and removing the catheter from the ascending aorta in order to prevent excessive trauma to the exterior and interior of the vessel wall.

Figure 11:
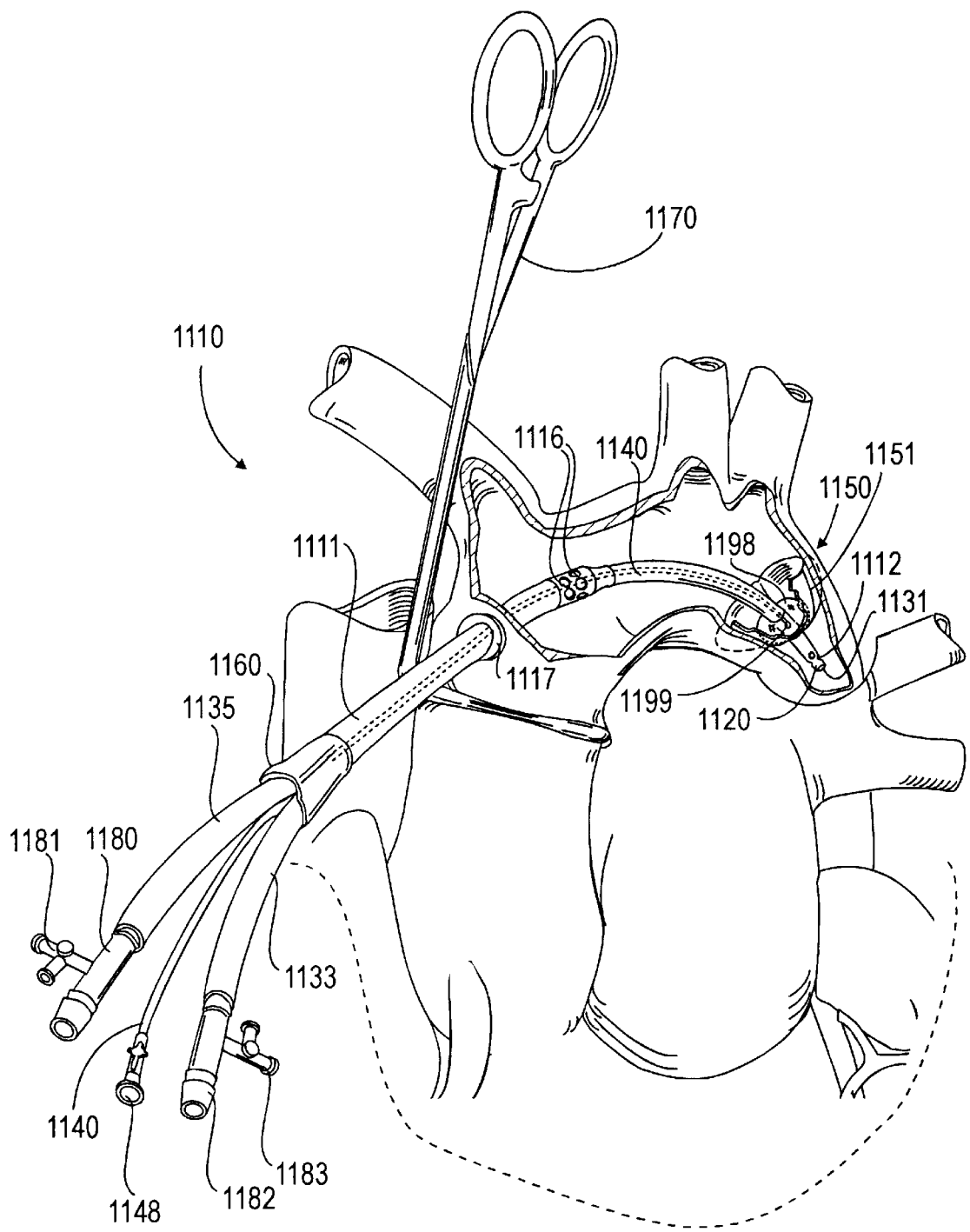

FIG. 11 shows a fifth embodiment of the present invention where the peripheral flow control valve regulator 1150 is actively deployed by a small actuating balloon 1198 which is inflatable through an inflation lumen 1140 extending through the elongated catheter shaft 1111 and terminating at inflation ports 1199. In alternate embodiments it is possible to have several actuating balloons 1198, for example, an actuating balloon 1198 to correspond with each individual leaflet 1151 of the peripheral flow control valve regulator. Nevertheless, hydraulic inflation of the actuating balloon 1198 will lift the valve leaflets 1151 away from the elongated catheter shaft 1111. Inflation of the small actuating balloon 1198 in certain embodiments can create the initial expansion of the valve leaflet 1151, after which positive pressure flow downstream of the cross clamp 1170 further expands the leaflet to at least partially occlude the descending aorta. Alternatively, the small actuating balloon 1198 maybe designed to completely actuate the valve leaflet 1151 to the desired diameter based on an increase in inflation volume to correspond to the desired diameter.

FIG. 12 depicts the peripheral flow control valve regulator 1050 of FIG. 11 in the undeployed state wherein the valve leaflets 1251 have a low profile around the catheter shaft 1211 creating a smooth outer surface when the small actuating balloon 1298 is uninflated. This low profile is especially beneficial when inserting and removing the catheter from the ascending aorta in order to prevent excessive trauma to the exterior and interior of the vessel wall.

Figure 13:
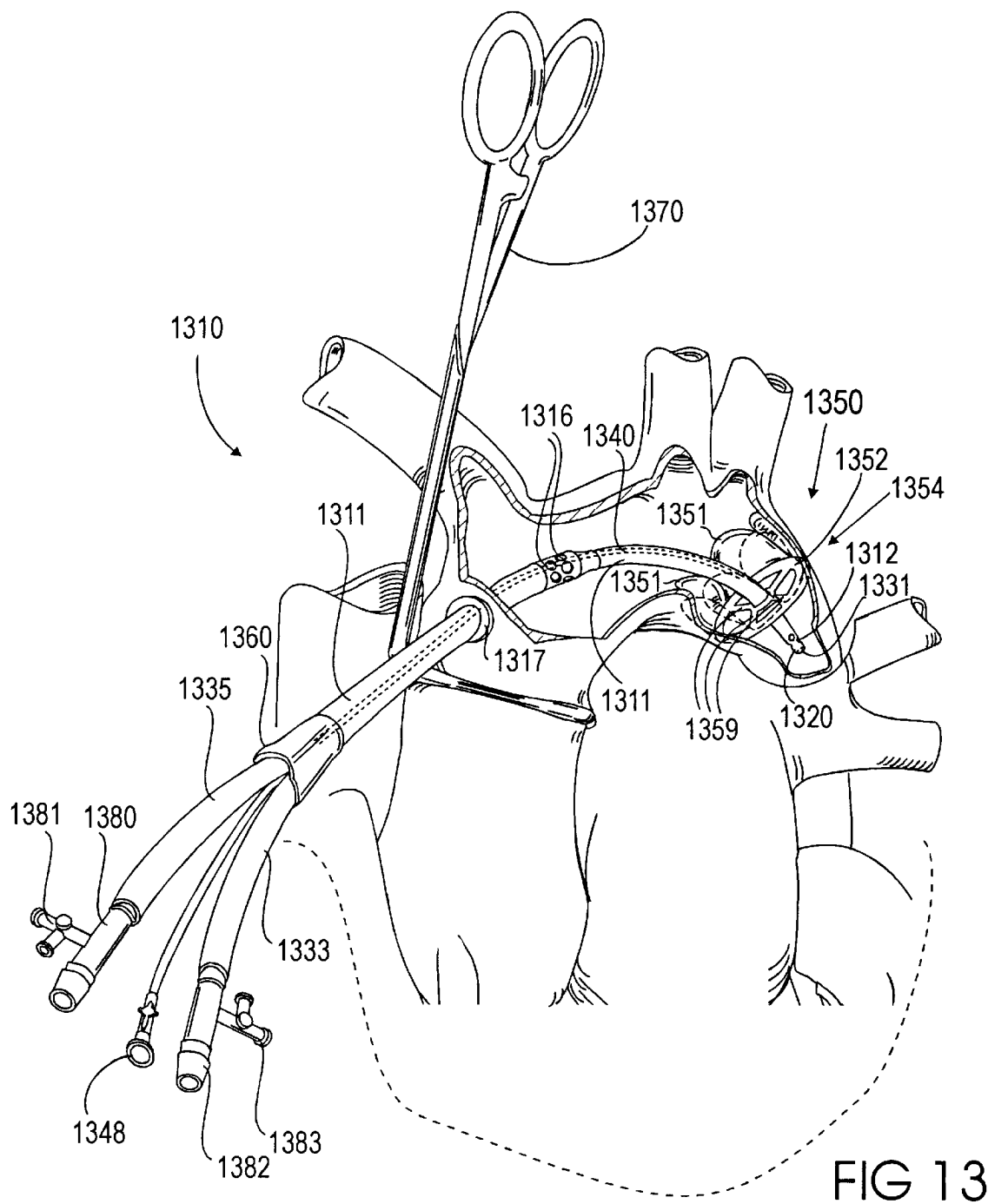
FIG. 13 is a schematic diagram showing a sixth embodiment of the aortic catheter of the present invention having a selectively deployable central flow control valve regulator.

FIG. 13 is a schematic diagram showing a sixth embodiment of the aortic catheter 1310, having a flow control regulator in the form of a selectively deployable central flow control valve regulator 1350 configured for antegrade deployment via an aortotomy incision in the ascending aorta. In this exemplary embodiment, the flow control regulator 1350 would preferably be in the form of a retrograde, central flow valve, as described in commonly owned, U.S. Pat. Nos. 5,827,237, 5,833,671 and commonly owned, copending patent application Ser. No. 08/664,360, which have previously been incorporated by reference. The central flow control valve regulator 1350 is constructed with a selectively expandable skeleton structure 1354 that is mounted on the catheter shaft 1311. In this exemplary embodiment, the skeleton structure 1354 has an inflatable outer rim 1352 supported on the catheter shaft 1311 by a plurality of inflatable radial spokes 1351. One or more valve leaflets 1359 (shown in the open position for clarity in FIG. 13) are pivotally attached to the outer rim 1352 or the radial spokes 1351 of the skeleton structure 1354. The leaflets 1359 of the central flow valve tend to pivot inward closing the valve in response to positive perfusion pressure in the aortic arch downstream of the cross clamp 1370.

FIGS. 14 through 16 illustrate a seventh embodiment of the aortic catheter of the present invention wherein the central flow control valve regulator 1450 is actively deployed by using a second catheter or tube. In addition to being used as a deployment mechanism, the second catheter or tube may have a separate valve regulator or occlusion balloon mounted thereon to eliminate the use of an external aortic cross clamp. The outer rim 1452 is attached to the spokes 1459 and the spokes 1459 are attached to the inferring 1451 of the skeleton structure 1354. The valve leaflets 1451 are deflated and folded or collapsed around the catheter shaft 1411. Deployment, depicted in FIGS. 15 and 16 sequentially, may be performed by pulling back the outer tube 1470, exposing the skeleton structure, once proper position has been established and deployment is desired. The skeleton structure 1454 is then inflated through the actuation lumen 1440 expanding the outer rim 1452 and spokes 1451 as shown in FIG. 16. When the central flow control regulator 1450 is fully deployed, the outer rim 1452 of the skeleton structure 1454 is actuated outward toward the vessel wall to at least partially occlude the vessel as illustrated in FIG. 13.

Figure 17:
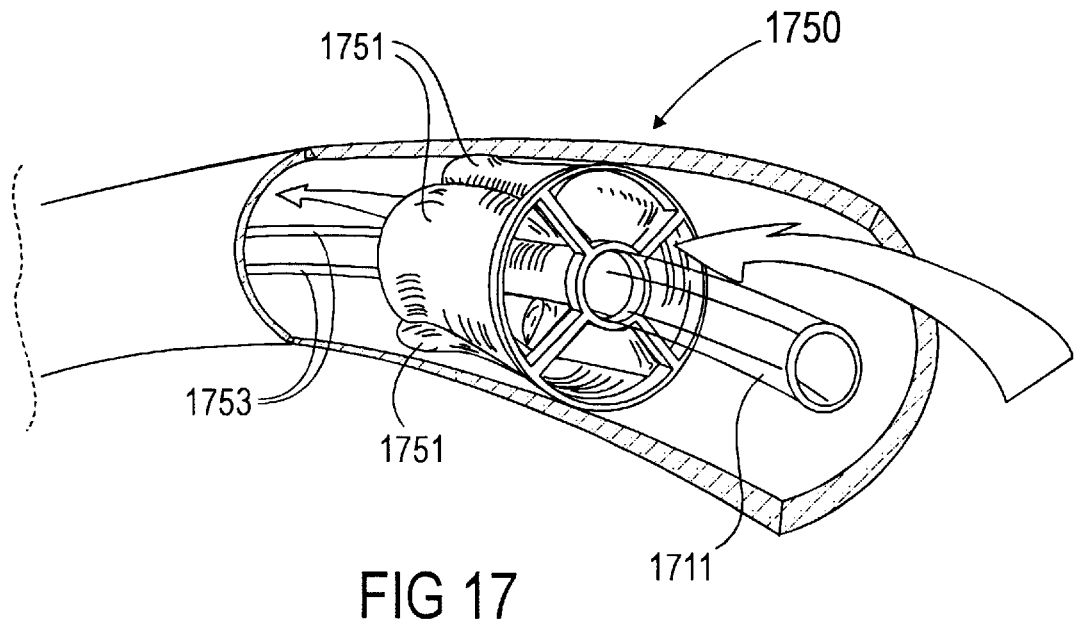
FIGS. 17 and 18 are cutaway illustrations of an eighth embodiment of the present invention where the central flow control valve regulator is mechanically deployed by one or more actuation wires.
Figure 18:
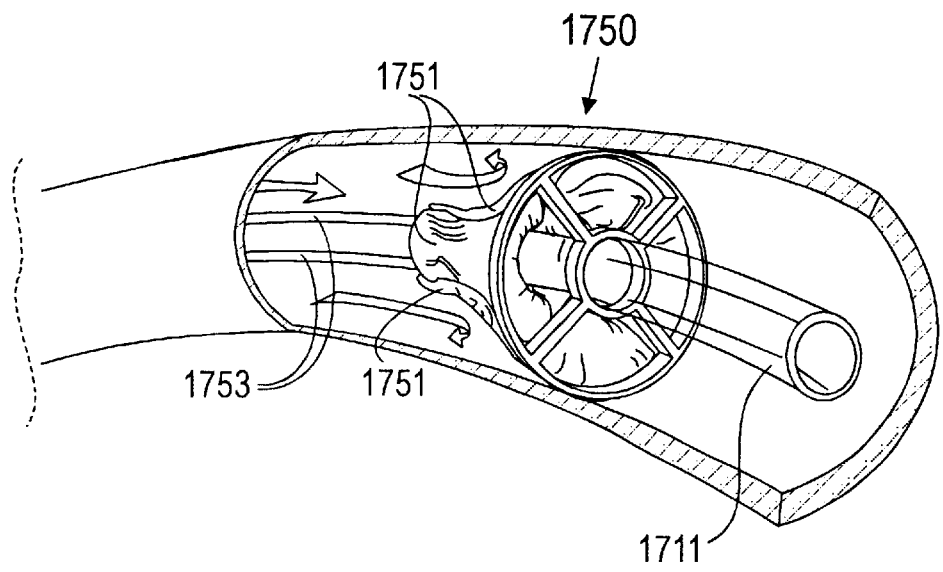

FIGS. 17 and 18 illustrate an eighth embodiment of the present invention, wherein the central flow control valve regulator 1750 is mechanically deployed by one or more actuation wires 1753 extending through the elongated catheter shaft 1711 and attached to the valve leaflets 1751. The central flow control valve regulator 1750 has an expanded or deployed state as shown in FIGS. 17 and 18. FIG. 17 illustrates the central flow control valve regulator 1750 in an open position, and FIG. 18 illustrates the deployed central flow control valve 1750 in the closed position. In the closed position, the central flow control valve regulator leaflets 1751 pivot inward in response to positive pressure on the downstream side of the aortic cross clamp.

Whereas a particular embodiment of the invention has been described above, for purposes of illustration, it will be understood by those skilled in the art that numerous variations of the details may be made without departing from the invention as defined in the appended claims.

What is claimed is:

1. An aortic catheter for segmenting and selectively perfusing a patient's aorta comprising:
    (a) an elongated shaft having a proximal end, a distal end and a length sufficient to be inserted into an ascending aorta and guided transluminally in an antegrade direction such that said distal end is positioned in a descending aorta when in the operative position and said proximal end resides external to the patient when in an operative position;
    (b) a proximal portion of said elongated shaft having an inner coil reinforced shaft whose internal diameter defines a corporeal perfusion lumen and an outer coil reinforced shaft, said inner coil reinforced shaft and said outer coil reinforced shaft configured in a coaxial relationship such that an annular space is created therebetween;
    (c) an arch perfusion lumen defined by said annular space terminating as at least one arch perfusion port positioned along the length of said elongated shaft;
    (d) a distal portion of said elongated shaft defined by said inner coil reinforced shaft and terminating as at least one or more corporeal perfusion ports;
    (e) a flow control regulator positioned proximal to said distal end and distal to said at least one arch perfusion ports, said flow control regulator sized and configured to at least partially occlude the aorta; and
    (f) a distal tip configured for insertion into the ascending aorta.

2. The aortic catheter of claim 1, wherein said elongated shaft is from 4 to 30 cm in length.

3. The aortic catheter of claim 1, wherein said corporeal perfusion lumen is connected to a ⅜ inch to ¼ inch barb reducer for connection to a perfusion pump.

4. The aortic catheter of claim 3, wherein said barb connector is coupled to a luer fitting for withdrawing fluid samples and injecting medications.

5. The aortic catheter of claim 1, wherein said arch perfusion lumen is connected to a ¼ inch barb connector for connection to a perfusion pump.

6. The aortic catheter of claim 5, wherein said barb connector is coupled to a luer fitting for monitoring perfusion pressure.

7. The aortic catheter of claim 1, wherein said inner coil reinforced shaft has an internal diameter of approximately 0.025" to 0.3".

8. The aortic catheter of claim 1, wherein said outer coil reinforced shaft has an internal diameter of approximately 0.15" to 0.35".

9. The aortic catheter of claim 1, wherein said corporeal perfusion lumen is sized and configured to communicate blood flow at a flow rate of approximately 0.5 L/min to 8 L/min with a pressure drop of approximately 0 mm Hg to 300 mm Hg.

10. The aortic catheter of claim 1, wherein said arch perfusion lumen is sized and configured to communicate blood flow at a flow rate of approximately 0.1 L/min to 3 L/min with a pressure drop of approximately 0 mm Hg to 300 mm Hg.

11. The aortic catheter of claim 1, wherein the combined flow rate of the arch perfusion lumen and the corporeal perfusion lumen is of approximately 0.6 L/min to 10 L/min with a pressure drop approximately of 0 mm Hg to 300 mm Hg.

12. The aortic catheter of claim 1, further comprising an actuation lumen, said actuation lumen having a proximal end and a distal port in fluid communication with said flow control regulator.

13. The aortic catheter of claim 12, wherein said flow control regulator is a balloon.

14. The aortic catheter of claim 13, wherein said balloon is made of a material selected from the group consisting of polymers and elastomers.

15. The aortic catheter of claim 13, wherein said balloon has an inflated outer diameter of approximately 0.5 to 4.0 cm.

16. The aortic catheter of claim 13, wherein said balloon has a radiopaque marker positioned within said balloon.

17. The aortic catheter of claim 1, wherein said flow control regulator is in the form of an actively deployed peripheral flow control valve regulator.

18. The aortic catheter of claim 1, wherein said flow control regulator is in the form of an actively deployed central flow control valve regulator.

19. The aortic catheter of claim 1, wherein said flow control regulator is in the form of an actively deployed peripheral flow control valve regulator with at least one actuating balloon.

20. The aortic catheter of claim 1, wherein said flow control regulator is a passively deployed peripheral flow control valve regulator.

21. The aortic catheter of claim 20, wherein said passively deployed peripheral flow control valve regulator has at least one leaflet.

22. The aortic catheter of claim 1, wherein said flow control regulator is a passively deployed central flow control valve regulator.

23. The aortic catheter of claim 1, wherein said distal tip is formed of a temperature sensitive material.

24. The aortic catheter of claim 1, wherein said elongated shaft has a curvature configured to conform to a patient's aortic arch anatomy.

25. The aortic catheter of claim 1, wherein said at least one arch perfusion port comprises from 1 to 16 external holes.

26. The aortic catheter of claim 1, wherein said at least one corporeal perfusion port comprises from 1–8 external holes.

* * * * *